United States Patent [19]

Abraham et al.

[11] Patent Number: 4,751,244
[45] Date of Patent: Jun. 14, 1988

[54] COMPOUNDS USEFUL IN TREATING SICKLE CELL ANEMIA

[75] Inventors: Donald J. Abraham, Murrysville; Otto W. Woltersdorf, Jr., Chalfont; Edward J. Cragoe, Jr., Lansdale, all of Pa.

[73] Assignees: Merck & Co., Inc., Rahway, N.J.; The University of Pittsburgh

[21] Appl. No.: 44,268

[22] Filed: Apr. 30, 1987

Related U.S. Application Data

[63] Continuation of Ser. No. 848,079, Apr. 4, 1986, abandoned.

[51] Int. Cl.$^4$ ............................................. A61K 31/195
[52] U.S. Cl. ................................... 514/563; 514/571; 514/815; 562/434; 562/435; 562/437
[58] Field of Search ...................... 514/563, 571, 815; 562/434, 435, 437

[56] References Cited

U.S. PATENT DOCUMENTS

| | | | |
|---|---|---|---|
| 3,409,661 | 11/1968 | Schultz et al. | 562/434 |
| 3,445,503 | 5/1969 | Schultz et al. | 562/434 |
| 3,860,639 | 1/1975 | Schultz | 562/434 |

Primary Examiner—James H. Reamer
Attorney, Agent, or Firm—Melvin Winokur; Joseph F. DiPrima; R. Brent Olson

[57] ABSTRACT

The present invention is directed to compounds of the general formula I and pharmaceutically acceptable salts thereof:

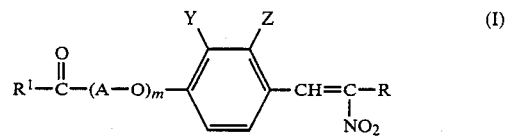

wherein:
$R^1$=HO or HOOC(CH$_2$)$_x$CHR$^2$NH—;
$R^2$=H, lower alkyl, benzyl or —CH$_2$OH;
x=0 or 1;
A=—(CH$_2$)$_n$— or

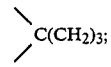

n=1 to 5; and
Y=H, Cl or OCH$_3$
Z=H or Cl
m=0 or 1
R=lower alkyl;

with the proviso that where $R^1$=OH, Y is H or Cl and m is 1, n is 4 or 5.

The present invention is also directed to an antisickling pharmaceutical carrier and an antisickling agent of the general formula (I) (without the proviso) and pharmaceutically acceptable salts thereof.

23 Claims, No Drawings

COMPOUNDS USEFUL IN TREATING SICKLE CELL ANEMIA

CROSS REFERENCE TO RELATED APPLICATION

This application is a continuation of applicant's co-pending application Ser. No. 848,079, filed Apr 4, 1986, now abandoned.

BACKGROUND OF THE INVENTION

This invention relates to compounds useful in treating sickle cell anemia and, more specifically, it relates to a method of resisting sickling of sickle hemoglobin in a sickle cell anemia patient.

The following references disclose analogues of the claimed compounds for use as diuretics: U.S. Pat. Nos. 3,409,661 and 3,445,503; Journal of Medicinal Chemistry, 19, 783 (1976); and Cragoe, Jr., E. J., Ed., Diuretics: Chemistry, *Pharmacology and Medicine,* John Wiley and Sons, New York 1983, in particular pages 222-227.

Sickle cell anemia is a hereditary blood disease which primarily afflict people of African, Mediterranean and Mideastern origin and their descendants. The anemia results from the physical aggregation of a mutant hemoglobin protein constituent in red blood cells. This aggregation results in a distortion in shape of deoxygenated red blood cells and causes impairment of flow of the blood through the capillaries (sickle cell "crises"). As the principal function of hemoglobin is to transport oxygen from the lungs to body tissues, efficient flow of oxygen throughout the body's tissues is impeded by the anemia due to a lower number of red blood cells. Sickle cell anemia also may have an indirect effect on the heart, lungs, kidneys, spleen, bones and brain. Sickle cell anemia crises can be extremely painful, can result in infections such as pneumonia, can result in skin ulceration, can contribute to strokes and seizures in the afflicted individuals and can also result in the development of chronic bone infections.

In general, the result of the differences between cells containing hemoglobin A, the normal hemoglobin, and hemoglobin S, the sickle cell hemoglobin, is that in the deoxygenated state the former cell is generally flexible and biconcave discoid in shape, while the latter is more rigid and crescent shaped and typically has pointed ends. This rigidity and distortion in shape causes the cells to be lodged in the capillary. Hemoglobin molecules contain two beta polypeptide chains and two alpha polypeptide chains. In the sickle cell hemoglobin, a mutation is present in the beta chains. More specifically, the sixth amino acid of each beta chain is changed from glutamic acid to valine. As a result of this mutation, hemoglobin S upon deoxygenation polymerizes and causes the cell to assume the elongated, sickle-like configuration. As the sickle cells have a much shorter life span than normal red cells, the body depletes the sickle cell more quickly thereby creating an anemic condition.

Electrophoresis is one of the well established laboratory tests employed in diagnosing sickle cell anemia. Electrophoresis tests determine whether an individual has sickle cell anemia (homozygous) or merely the sickle cell trait (heterozygous). The latter refers to an individual not having the disease but having the capability of transmitting the disease to offspring if mated to another heterozygote.

One major assay for evaluating antisickling agents involves measuring their effect on increasing the concentration at which sickle hemoglobin forms a gel. This is called the solubility or $C_{sat}$ assay.

Another well established laboratory test employed for determining the potential effectiveness of an antisickling agent is by determining the oxygen-disassociation curve. When a graph is plotted of the percentage saturation of hemoglobin with oxygen (ordinate) against the partial pressure of oxygen, sometimes called the oxygen tension (abscissa) a characteristic sigmoid curve is obtained. With respect to the curve obtained with whole blood from normal adults, that obtained with whole blood from sickle-cell anemia sufferers is displaced to the right with a loss of sigmoidicity. That is to say, the hemoglobin in the sickle-cell erythrocytes appears to have a reduced oxygen affinity compared with that in the normal erythrocytes, a higher oxygen tension being required to produce a given percentage saturation. (With whole blood from individuals having the sickle-cell trait the curve is not significantly displaced from the normal).

The compounds of this invention are effective in both increasing sickle hemoglobin solubility toward more normal values ($C_{sat}$ assay) and in left-shifting (normalizing) the oxygen disassociation curve.

Treatment for the various complications which have resulted from sickle cell anemia are known and should be distinguished from prophylactic treatment which is unknown and would eliminate the occurrence of the complications and adverse symptoms. Currently, symptomatic treatment is available. For example, one can treat the symptoms by using analgesics for pain, or antibiotics for infection, but these approaches do not arrest the underlying sickling phenomena.

There remains, therefore, a very real and substantial need for a treatment method which minimizes the adverse consequences of sickle cell anemia by directly inhibiting the underlying cause of sickle cell crises.

The present invention has met the above-described need by providing a method which preferably involves administering to a person a therapeutically effective dosage of a compound of this invention. This dosage is administered by the compound being reacted extracorporeally with the patient's own blood or the agent may be given orally. In the former approach the agent is preferably administered to stored blood samples taken from patients and then the blood is readministered.

It is an object of the present invention to provide a method of treating a sickle cell anemia patient's blood so as to reduce undesired sickle cell crises.

It is another object of the present invention to provide an effective means for resisting undesired sickling of hemoglobin in sickle cell anemia patients.

DESCRIPTION OF THE INVENTION

The instant invention is directed to compounds of the general formula (I) and pharmaceutically acceptable salts thereof:

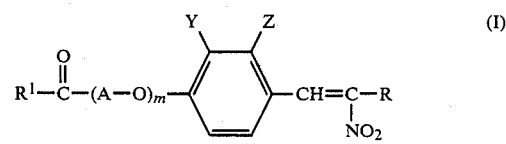

wherein:

$R^1$=HO or HOOC(CH$_2$)$_x$CHR$^2$NH—;
$R^2$=H, lower alkyl, benzyl or —CH$_2$OH, preferably H or lower alkyl (C$_{1-4}$), most preferably H;
x=0 or 1;
A=—(CH$_2$)$_n$— or

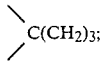

n=1 to 5; and
Y=H, Cl or OCH$_3$
Z=H or Cl
m=0 or 1
R lower alkyl, preferably C$_{1-4}$;
with the proviso that where $R^1$=OH, Y is H or Cl and m is 1, then n is 4 or 5.

The present invention is also directed to an antisickling pharmaceutical carrier and an antisickling agent of the general formula (I) (without the proviso) and pharmaceutically acceptable salts thereof.

The present invention is also directed to a method of treating a person for sickle cell anemia comprising administering to the person a therapeutically effective dosage of a compound of the general formula and pharmaceutically acceptable salts thereof:

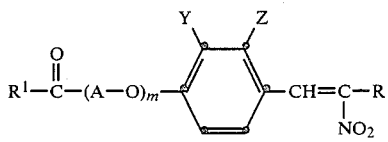

wherein:
$R^1$=HO or HOOC(CH$_2$)$_x$CHR$^2$NH—;
$R^2$=H, lower alkyl, benzyl or —CH$_2$OH;
X=0 or 1;
A=—(CH$_2$)$_n$— or

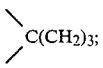

n=1 to 5; and
Y=H, Cl or OCH$_3$
Z=H or Cl
m=0 or 1
R lower alkyl.

The compounds of the above formula as defined, may be used in medicine in the palliation of haemoglobinopathies and in particular for alleviating the symptoms of sickle-cell anemia and mitigating the sufferings of those having the condition. The compounds may be used both on a regular maintenance basis and for the relief of acute crisis states.

The compounds may be administered to the human recipient by a route selected from oral, parenteral (including subcutaneous, intradermal, intramuscular and intravenously rectal and extracorporeally. The size of an effective palliative dose of a compound will depend upon a number of factors including the identity of the recipient, the type of haemoglobinopathy involved, the severity of the condition to be treated and the route of adminstration and will ultimately be at the discretion of the attendant physician.

The compounds of the invention wherein $R^1$ (of Structure I) is OH (Structure Ia) are prepared as follows:

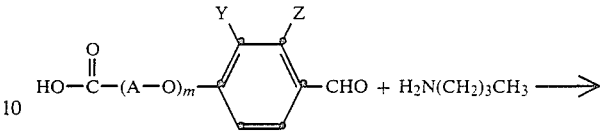

(III)

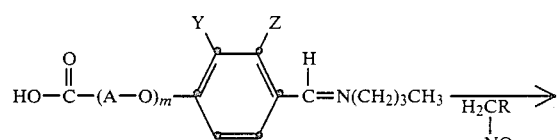

(II)

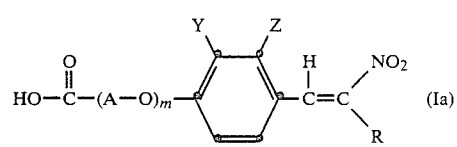

A benzaldehyde of Structure III is heated with butylamine in a solvent such as benzene or toluene until the water that is generated is removed by distillation, thus forming a Schiff base of Structure II. Addition of a nitroalkane of type RCH$_2$NO$_2$ and heating the mixture gave the desired compound of Structure Ia.

The intermediate compounds of Formula IIIa (where m=1) are prepared as follows for compounds where A=(CH$_2$)$_n$, or

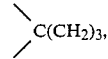

where n=1, 3, 4 or 5.

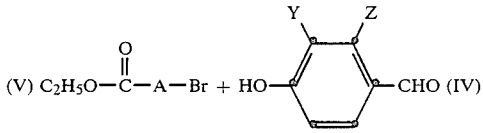

DMF | K$_2$CO$_3$

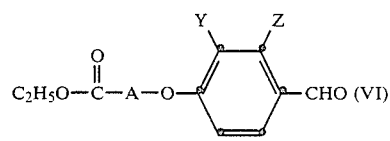

1. NaOH + H$_2$O
2. HCl

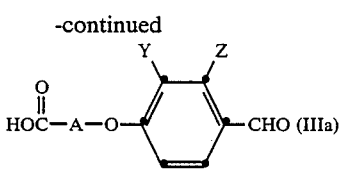

A phenol of Formula IV is reacted with a bromo ester of Formula V to produce an ester of Formula VI. The reaction is conducted in any one of several solvents, such as N,N-dimethylformamide (DMF) or 1-methyl-2-pyrrolidinone in the presence of a base, such as potassium carbonate or sodium carbonate. The reaction temperature is generally of 25° to 100° C., preferably at 55°–60° C. for a period of one to 48 hours, preferably 10–20 hours.

The esters of Formula VI are converted to the corresponding carboxylic acids of Formula IIIa by saponification with aqueous sodium hydroxide followed by acidification. Saponification is conveniently conducted in the presence of the N,N-dimethylformamide solvent used for making the ester. Saponification is generally complete within one to five hours when the reaction temperature is in the range of 75°–100° C.

When A is —(CH$_2$)$_2$— and Y and Z are Cl, the compounds of Formula IIIb are prepared as follows:

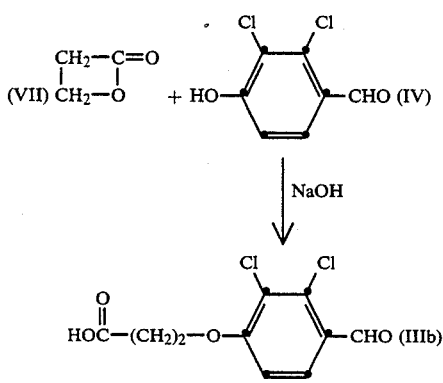

Reaction of a phenol of Formula IV with β-propiolactone (VII) in water and a base, such as potassium hydroxide or sodium hydroxide gives the product of Formula IIIb. The product is isolated by acidification extracting with ether, extracting the ether layer with aqueous sodium bicarbonate followed by acidification of the aqueous extract with hydrochloric acid.

The compounds of the invention wherein R$^1$ is HOOC(CH$_2$)$_x$CHR$^2$NH— (formula Ib) are prepared as follows:

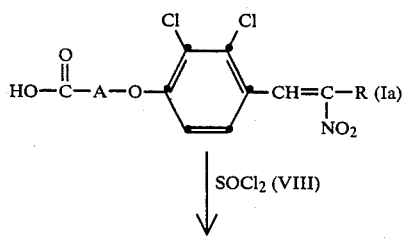

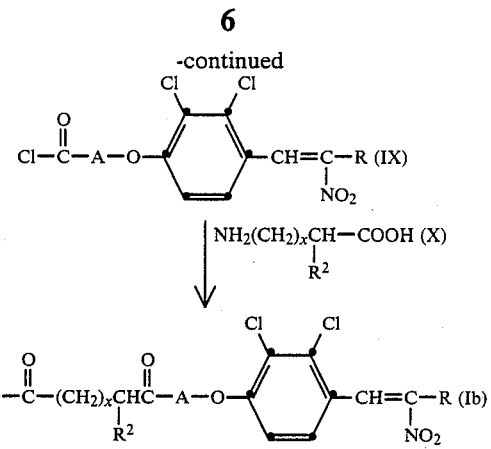

A compound of Formula IX is prepared by treating a compound of Formula Ia with thionyl chloride (VIII) or similar reagent in an inert solvent such as benzene, toluene, methylene chloride, carbon tetrachloride and the like. The reaction is conducted at temperatures of 40° C. to that of the boiling point of the solvent, preferably, if possible, in the range of 60°–80° C. for periods of time of 30 minutes to 6 hours. During this time the hydrogen chloride generated during the reaction is evolved.

The reaction of a compound of Formula IX with two moles of a compound of an amino acid of Formula X gives a compound of Formula Ib.

It should be noted that when R$^2$ of Formula Ib is other than H, the product of Formula Ib can well be either racemic or the R- or S-enantiomer depending on the structure of Formula X used in the reaction.

The preferred salts are the pharmaceutically acceptable salts such as sodium, potassium, ammonium and the like.

As implied earlier, the compounds of this invention may be administered by a variety of established methods, including intravenously, intramuscularly, subcutaneously, orally and extracorporeally. The precise mode of administration is left to the discretion of the practitioner. The option of extracorporeal administration is unique to the therapeutic approach of this invention. Since the entity to which therapy is administered is the erythrocytes of the patient, blood can be removed from the patient, treated with the drug and returned to the patient after the desired interaction between the drug and the erythrocytes has occurred. Before returning the drug-treated blood, the excess (unreacted drug) may be removed, thus reducing any ancillary effects that this excess might cause.

The compounds of formula I are utilized by formulating them in a composition such as tablet, capsule or elixir for oral administration. Sterile solutions or suspensions can be used for parenteral administration. About 70 μg to 500 mg of a compound or mixture of compounds of formula I, or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in the composition is such that dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose, or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise enhance the pharmaceutical elegance of the preparation. For instance, tablets may be coated with shellac, sugar or the like. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a conventional vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

Since an individual patient may present a wide variation in severity of symptoms and each drug has its unique therapeutic characteristics, it is up to the practitioner to determine the patient's response to treatment and vary the dosages accordingly. A recommended dose range is from 100 μg/kg to 15 mg/kg as a primary dose and then, if necessary a sustaining dose equal to half to equal the primary dose may be administered every 12 to 24 hours.

When the compounds of this invention are employed for extracorporeal treatment of blood, it is generally convenient to use a water soluble salt of the compound which may be made isotonic by addition of sodium chloride. The concentration of the compound which is used for this purpose is generally in the range of 0.1 to 10 mM with a range of 1 to 3 mM being more commonly used.

The following examples are included to illustrate the synthesis of representative compounds of Formula I, the preparation of representative dosage forms and the preparation of sterile solutions for use in the extracorporeal treatment of the blood of patients with sickle cell anemia. It is intended that the specification and examples be considered as exemplary only, with the true scope and spirit of the invention being indicated by the claims of the invention.

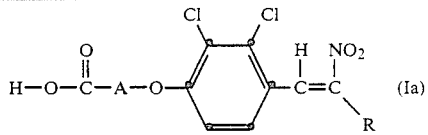 (Ia)

| Example | A | R |
|---|---|---|
| 1 | (CH₂)₃ | C₂H₅ |
| 2 | (CH₂)₂ | CH₃ |
| 3 | (CH₂)₃ | CH₂CH₂CH₃ |
| 4 | (CH₂)₄ | C₂H₅ |
| 5 | (CH₂)₅ | C₂H₅ |
| 6 | 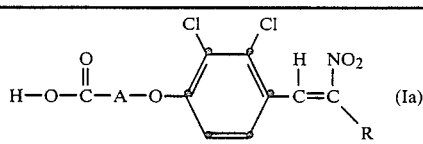 C(CH₂)₃ | C₂H₅ |

-continued (Ia)

| Example | A | R |
|---|---|---|
| 7 | C(CH₂)₃ | CH₂CH₂CH₃ |
| 8 | (CH₂)₃ | CH(CH₃)₂ |

(E) after the Example number below refers to the fact that the vinyl hydrogen is cis to the nitro group.

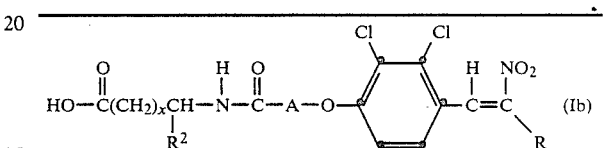 (Ib)

| Example | X | R² | A | R |
|---|---|---|---|---|
| 9 | 0 | H | (CH₂)₃ | C₂H₅ |
| 10 | 0 | CH₃ | (CH₂)₃ | C₂H₅ |
| 11 | 0 | CH₂CH(CH₃)₂ | (CH₂)₃ | C₂H₅ |
| 12 | 0 | CH₂OH | (CH₂)₃ | C₂H₅ |
| 13 | 0 | CH₂C₆H₅ | (CH₂)₃ | C₂H₅ |
| 14 | 0 | H | (CH₂)₃ | (CH₂)₂CH₃ |
| 15 | 0 | H | C(CH₂)₃ | C₂H₅ |
| 16 | 0 | H | (CH₂)₂ | C₂H₅ |
| 17 | 0 | H | (CH₂)₄ | C₂H₅ |
| 18 | 0 | H | (CH₂)₅ | C₂H₅ |
| 19 | 1 | H | C(CH₂)₃ | C₂H₅ |

The (E) that appears in the name of each Example below refers to the fact that the vinyl hydrogen atoms is cis to the nitro group. The S refers to the absolute conformation of the amino acid from which the compounds were derived. S is the form in which most amino acids exist. The + or − in parentheses refers to the optical rotation of the amino acid.

EXAMPLE 1

(E)-4-[2,3-dichloro-4-(2-nitro-1-butenyl)phenoxy]-butyric acid

Step A: 4-(2,3-dichloro-4-formylphenoxy)butyric acid

A mixture of 2,3-dichloro-4-formylphenol (5.73 g., 0.03 mole), ethyl 4-bromobutyrate (11.7 g., 0.06 mole) and potassium carbonate (8.28 g., 0.06 mole) in dimethylformamide (25 ml.) is heated at 50°–60° C. for 1½ hours. Water (50 ml.) is added and the mixture is extracted with ether. The ether extract is dried and evaporated. To the residue is added a solution composed of 48 ml. of 40% sodium bisulfite and 12 ml. of alcohol. The precipitated 4isulfite addition compound then is washed with alcohol and ether. The solid is suspended in water heated in a steam bath. An oily layer of the free aldehyde is formed. The hot water then is decanted and the oily layer is extracted with ether and the ether evaporated. The residue is heated to 80° C. in a mixture of potassium hydroxide (2.8 g.), methanol (30 ml.) and water (5 ml.), the resulting solution is evaporated to dryness and the residue dissolved in water. Upon acidification a solid separates. The solid is crystallized from benzene to obtain 2.9 g. of 4-(2,3-dichloro-4-formylphenoxy)butyric acid, M.P. 147°–148° C.

Analysis for $C_{11}H_{11}Cl_2O_4$: Calculated, C, 47.67; H, 3.64; Cl, 25.59. Found: C, 47.70; H, 3.60; Cl, 25.65.

Step B: 4-[2,3-dichloro-4-(2-nitro-1-butenyl)phenoxy]butyric acid

The 4-(2,3-dichloro-4-formylphenoxy)butyric acid (2.7 g., 0.01 mole) and n-butylamine (2.2 g., 0.03 mole), in benzene, are refluxed for three hours or until no more water is evolved. The benzene is evaporated and then acetic acid (12 ml.) and 1-nitropropane (3.6 g., 0.04 mole) are added. The mixture is heated to boiling and then poured onto ice. The yellow solid that separates is crystallized from ethanol to obtain 1.3 g. of 4-[2,3-dichloro-4-(2-nitro-1-butenyl)phenoxy]butyric acid, M.P. 155°–156.5° C.

Analysis for $C_{14}H_{15}Cl_2NO_5$; Calculated, C, 48.29; H, 4.50; N, 4.02. Found: C, 48.51; H, 4.42; N, 4.30.

EXAMPLE 2

(E)-3-[2,3-dichloro-4-(2-nitro-1-propenyl)phenoxy]propionic acid

Step A: 3-(2,3-dichloro-4-formylphenoxy)propionic acid 2,3-dichloro-4-hydroxybenzaldehyde (38.2 g., 0.2 mole) is dissolved in a 10% sodium hydroxide solution (200 ml.). The solution is heated to boiling and β-propiolactone (144 g., 2.0 moles) is added dropwise at such a rate as to keep the solution boiling. During the addition 10% sodium hydroxide solution is added in portions to maintain an alkaline mixture. Then the solution is cooled and acidified. The precipitated material is dissolved in ether and the product is extracted into a 5% sodium bicarbonate solution. Acidification of the aqueous solution precipitates 3-(2,3-dichloro-4-formylphenoxy)propionic acid, which is purified by recrystallization from ethyl acetate.

Step B: (E)-3-[2,3-dichloro-4-(2-nitro-1-propenyl)phenoxy]propionic acid.

By following substantially the procedure described in Example 1, Step B, except that the 4-(2,3-dichloro-4-formylphenoxy)butyric acid used therein is replaced by an equimolar quantity of 3-(2,3-dichloro-4-formylphenoxy)propionic acid, and there is obtained (E)-3-[2,3-dichloro-4-(2-nitro-1-propenyl)phenoxy]propionic acid.

EXAMPLE 3

(E)-4-[2,3-dichloro-4-(2-nitro-1-pentenyl)phenoxy]butyric acid

By following substantially the procedure described in Example 1, Step B, except that the 1-nitropropane used therein is replaced by an equimolar quantity of 1-nitrobutane and there is obtained 4-[2,3-dichloro-4-(2-nitro-1-pentenyl)phenoxy]butyric acid.

EXAMPLE 4

(E)-5-[2,3-dichloro-4-(2-nitro-1-butenyl)phenoxy]pentanoic acid

Step A: 5-(2,3-dichloro-4-formylphenoxy)pentanoic acid

By following substantially the procedure described in Example 1, Step A, except that the ethyl 4-bromobutyrate used therein is replaced by an equimolar quantity of ethyl 5-bromovalerate and there is obtained 5-(2,3-dichloro-4-formylphenoxy)pentanoic acid.

Step B: (E)-5-[2,3-dichloro-4-(2-nitro-1-butenyl)phenoxy]pentanoic acid.

By following substantially the procedure described in Example 1, Step B, except that the 4-(2,3-dichloro-4-formylphenoxy)butyric acid, used therein is replaced by an equimolar quantity of 5-(2,3-dichloro-4-formylphenoxy)pentanoic acid, and there is obtained (E)-5-[2,3-dichloro-4-(2-nitro-1-butenyl)phenoxy]pentanoic acid.

EXAMPLE 5

(E)-6-[2,3-dichloro-4-(2-nitro-1-butenyl)phenoxy]hexanoic acid

Step A: 6-(2,3-dichloro-4-formylphenoxy)hexanoic acid

By following substantially the procedure described in Example 1, Step A, except that the ethyl 4-bromobutyrate used therein is replaced by an equimolar quantity of ethyl 6-bromohexanoate and there is obtained 6-(2,3-dichloro-4-formylphenoxy)hexanoic acid.

Step B: (E)-6-[2,3-dichloro-4-(2-nitro-1-butenylphenoxy]hexanoic acid

By following substantially the procedure described in Example 1, Step B, except that the 4-(2,3-dichloro-4-formylphenoxy)butyric acid used therein is replaced by an equimolar amount of 6-(2,3-dichloro-4-formylphenoxy)hexanoic acid and there is obtained (E)-6-[2,3-dichloro-4-(2-nitro-1-butenyl)phenoxy]hexanoic acid.

EXAMPLE 6

(E)-1-[2,3-dichloro-4-(2-nitro-1-butenyl)phenoxy]cyclobutane-1-carboxylic acid

Step A: 1-(2,3-dichloro-4-formylphenoxy)cyclobutane-1-carboxylic acid

By following substantially the procedure described in Example 1, Step A except that the ethyl 4-bromobutyrate is replaced by an equimolar quantity of ethyl 1-bromocyclobutanecarboxylate and there is obtained 1-(2,3-dichloro-4-formylphenoxy)cyclobutane-1-carboxylic acid.

Step B:
(E)-1-[2,3-dichloro-4-(2-nitro-1-butenyl)phenoxy]cyclobutane-1-carboxylic acid By following substantially the procedure described in Example 1, Step B, except that the 4-(2,3-dichloro-4-formylphenoxy)butyric acid used therein is replaced by an equimolar quantity of 1-(2,3-dichloro-4-formylphenoxy)cyclobutane-1-carboxylic acid.

EXAMPLE 7

(E)-1-[2,3-dichloro-4-(2-nitro-1-pentenyl)phenoxy]cyclobutane-1-carboxylic acid

By following substantially the same procedure described in Example 1, Step B except that the 4-(2,3-dichloro-4-formylphenoxy)butyric acid and 1-nitropropane are replaced by equimolar quantities of 1-(2,3-dichloro-4-formylphenoxy)cyclobutane-1-carboxylic acid (See Example 6, Step A) and 1-nitrobutane and there is obtained (E)-1-[2,3-dichloro-4-(2-nitro-1-pentenyl)phenoxy]cyclobutane-1-carboxylic acid

EXAMPLE 8

(E)-4-[2,3-dichloro-4-(3-methyl-2-nitro-1-butenyl)phenoxy]butyric acid

By following substantially the procedure described in Example 1, Step B except that the 1-nitropropane used therein is replaced by and equimolar quantity of 1-nitro-2-methylpropane and there is obtained (E)-4-[2,3-dichloro-4-(2-methyl-2-nitro-1-butenyl)phenoxy]butyric acid.

EXAMPLE 9

N-{(E)-4-[2,3-Dichloro-4-(2-nitro-1-butenyl)phenoxy]butyryl}glycine (E)-4-[2,3-Dichloro-4-(2-nitro-1-butenyl)phenoxy]butyric acid (20.89 g, 0.06 mole) is dissolved in dry benzene (45 ml) and thionyl chloride (19.04 g, 0.12 mole) and the mixture stirred and refluxed for 75 minutes. The volatile materials are removed by evaporation at reduced pressure and the residue, which consisted of (E)-4-[2,3-dichloro-4-(2-nitro-1-butenyl)phenoxy]butyryl chloride, is dissolved in dry tetrahydrofuran (50 ml).

To a stirring suspension of finely ground glycine (6.01 g, 0.08 mole) in tetrahydrofuran (50 ml) is added, dropwise, the solution of E-4-[2,3-dichloro-4-(2-nitro-1-butenyl)phenoxy]butyryl chloride over a period of 15 minutes. The mixture is stirred at ambient temperature for 2.25 hours and then at reflux for one hour. The mixture is cooled, filtered and washed with tetrahydrofuran. The solid is suspended in water (60 ml), filtered, washed with water and dried to give 7.45 g of N-{(E)-4-[2,3-dichloro-4-(2-nitro-1-butenyl)phenoxy]butyryl}glycine.

EXAMPLE 10

N-{(E)-4-[2,3-Dichloro-4-(2-nitro-1-butenyl)phenoxy]butyryl}-S(+)-alanine

By carrying out the reaction essentially as described in Example 9, except that the glycine was replaced by an equimolar quantity of L-alanine, there was obtained N-{(E)-4-[2,3-dichloro-4-(2-nitro-1-butenyl)phenoxy]butyryl}-S(+)-alanine.

EXAMPLE 11

N-{(E)-4-[2,3-Dichloro-4-(2-nitro-1-butenyl)phenoxy]butyryl}-S(+)-leucine

By carrying out the reaction essentially as described in Example 9, except that the glycine is replaced by an equimolar quantity of S(+)leucine, there is obtained N-{(E)-4-[2,3-dichloro-4-(2-nitro-1-butenyl)phenoxy]butyryl}-S(+)-leucine.

EXAMPLE 12

N-{(E)-4-[2,3-Dichloro-4-(2-nitro-1-butenyl)phenoxy]butyryl}-S(+)-serine

By carrying out the reaction essentially as described in Example 9, except that the glycine is replaced by an equimolar quantity of L-serine, there is obtained N-{(E)-4-[2,3-dichloro-4-(2-nitro-1-butenyl)phenoxy]butyryl}-S(+)-serine.

EXAMPLE 13

N-}(E)-4-[2,3-Dichloro-4-(2-nitro-2-butenyl)phenoxy]butyryl}-S(−)-phenylalanine

By carrying out the reaction essentially as described in Example 9, except that the glycine is replaced by an equimolar quantity of L-phenylalanine, there is obtained N-{(E)-4-[2,3-dichloro-4-(2-nitro-1-butenyl)phenoxy]butyryl}-S(−)-phenylalanine.

EXAMPLE 14

N-{(E)-4-[2,3-Dichloro-4-(2-nitro-1-pentenyl)phenoxy]butyryl}glycine

By carrying out the reaction essentially as described in Example 9, except that the (E)-4-[2,3-dichloro-4-(2-methylenebutyryl)phenoxy]butyric acid is replaced by an equimolar quantity of (E)-4-[2,3-dichloro-4-(2-nitro-1-pentenyl)phenoxy]butyric acid, there is obtained N-{(E)-(4-[2,3-dichloro-4-(2-nitro-1-pentenyl)phenoxy]butyryl}glycine.

EXAMPLE 15

N-{(E)-1-[2,3-Dichloro-4-(2-nitro-1-butenyl)phenoxy]cyclobutane-1-carbonyl }glycine By carrying out the reaction essentially as described in Example 9, except that the (E)-4-[2,3-dichloro-4-(2-nitro-1-butenyl)phenoxy]acetic acid is replaced by an equimolar quantity of 1-[2,3-dichloro-(2-nitro-1-butenyl]cyclobutane-1-carboxylic acid, there is obtained N-{(E)-1-[2,3-dichloro-(2-nitro-1-butenyl)phenoxy]cyclobutane-1-carbonyl}glycine.

EXAMPLE 16

N-{(E)-3-[2,3-Dichloro-4-(2-nitro-1-butenyl)phenoxy]propionyl }glycine

By carrying out the reaction essentially as described in Example 9, except that the (E)-4-[2,3-dichloro-4-(2-nitro-1-butenyl)phenoxy]butyric acid is replaced by an equimolar quantity of (E)-3-[2,3-dichloro-(2-nitro-1-butenyl)phenoxy]propionic acid, there is obtained N-{(E)-3-[2,3-dichloro-4-(2-nitro-1-butenyl) phenoxy]propiony}glycine.

13

EXAMPLE 17

N-{(E)-5-[2,3-Dichloro-4-(2-nitro-1-butenyl)phenoxy]-pentanoyl}glycine

By carrying out the reaction essentially as described in Example 9, except that the (E)-4-[2,3-dichloro-4-(2-nitro-1-butenyl)phenoxy]butyric acid is replaced by an equimolar quantity of (E)-5-[2,3-dichloro-4-(2-nitro-1-butenyl)phenoxy]pentanoic acid, there is obtained N-{(E)-5-[2,3-dichloro-4-(2-nitro-1-butenyl) phenoxy]pentanoyl}glycine.

EXAMPLE 18

N-{(E)-5-[2,3-Dichloro-4-(2-nitro-1-butenyl)phenoxy]-hexanoyl}glycine

By carrying out the reaction essentially as described in Example 9, except that the (E)-4-[2,3-dichloro-4-(2-nitro-1-butenyl)phenoxy]butyric acid is replaced by an equimolar quantity of (E)-6-[2,3-dichloro-(2-nitro-1-butenyl)phenoxy]hexanoic acid, there is obtained N-{(E)-6-[2,3-dichloro-4-(2-nitro-1-butenyl)phenoxy]hexanoyl}glycine.

EXAMPLE 19

N-{(E)-1-[2,3-Dichloro-4-(2-nitro-1-butenyl)phenoxy]-cyclobutane-1-carbonyl}-3-aminopropionic acid By carrying out the reaction essentially as described in Example 9, except that the (E)-4-[2,3-dichloro-4-(2-nitro-1-butenyl)phenoxy]butyric acid is replaced by an equimolar quantity of (E)-1-[2,3-dichloro-4-(2-nitro-1-butenyl)phenoxy]cyclobutane-1-carboxylic acid and the glycine is replaced by an equimolar quantity of β-alanine, there is obtained N-{(E)-1-[2,3-dichloro-4-(2-nitro-1-butenyl)phenoxy]-cyclobutane-1-carbonyl}-3-aminopropionic acid.

EXAMPLE 20

(E) [4-(2-Nitro-1-propenyl)phenoxy]acetic Acid

Step A: Ethyl (4-formylphenoxy)acetate p-Hydroxybenzaldehyde (122 g, 1 mole), ethyl bromoacetate (167 g, 1 mole), potassium carborate (138 g, 1 mole) and acetone (500 ml) were united, stirred and refluxed for 3 hours. The reaction mixture was poured into crushed ice (2 kg). The solid that separates was removed by filtrations, washed with water, dried and recrystallized from ethanol to give 157 g of product, m.p. 41°-42° C.

Step B: Ethyl [4-(butyliminomethylene)phenoxy]acetate

Ethyl (4-formylphenoxy)acetate (104.1 g, 0.5 mole), butylamine (36.6 g, 0.5 mole) and benzene (400 ml) were united and refluxed in a flask equipped with a Dean-Stark water separator. After one hour, water ceased to separate. The heating was terminated after 6 hours and the mixture distilled. There was obtained 108.6 g of product boiling at 178°-181° C. at 0.5 mm Hg pressure.

Step C: Ethyl [4-(nitro-1-propenyl)phenoxy]acetate

Ethyl [4-(butyliminomethylene)phenoxy]-acetate (23.6 g, 0.1 mole), nitroethane (26 g, 0.35 mole) and acetic acid (75 ml) were united and heated to boiling. After standing for 30 minutes, the solution was chilled and poured with stirring into ice water (500 ml). The solid that separated upon cooling was removed by filtration, washed wtih water, dried and recrystallized from ethanol. The yield product was 22 g, m.p. 80°-82° C. Step D: (E) [4-(2-Nitro-1-propenyl)phenoxy]acetic acid Ethyl (E) [4-(2-nitro-1-propenyl)phenoxy]acetate (10 g, 0.0378 mole), glacial acetic acid (70 ml) water (50 ml) and concentrated hydrochloric acid (2 ml) were place in a flask and stirred and refluxed for 2 hours. The mixture was chilled in ice and the precipitate that formed removed by filtration, washed with cold ethanol and dried. Concentration of the filtrate to a volume of 50 ml and cooling yielded more product which was removed by filtration.

The combined products were recrystallized from a 50% mixture of water and ethanol to give (E)[4-(2-nitro-1-propenyl)phenoxy]acetic acid, m.p. 149°-151° C.

EXAMPLE 21

(E) 3-Chloro-4-(2-nitro-1-butenyl)benzoic acid

Step A: 3-Chloro-4-formylbenzoic acid

3-Chloro-4-formylbenzonitrile (16.5 g, 0.1 mole) was stirred and refluxed with concentrated hydrochloric (60 ml) for 16 hours. The mixture was cooled and the solid separated by filtration, washed with water and dried. The solid was treated with an aqueous sodium bicarbonate solution and filtered. The filtrate was acidified with dilute hydrochloric acid to give the desired product which was separated by filtration, washed with water and dried to give 7.25 g of material melting at 214°-215° C.

Step B: (E) 3-Chloro-4-(2-nitro-1-butenyl)benzoic acid

3-Chloro-4-formylbenzoic acid (5 g, 0.027 mole), butylamine (2 g, 0.027 mole) and benzene (75 ml) were refluxed for 2 hours using a flask fitted with a Dean-Stark water separator. The solvent was removed by distillation in vacuo to give 3-chloro-4-(butyliminomethylene) benzoic acid to which was added nitropropane (8.9 g, 0.1 mole) and acetic acid (21 ml). The mixture was refluxed for 10 minutes then cooled in ice. The mixture was treated with water and the solid that separated removed by filtration, washed with water, dried and recrystallized from a mixture of acetic acid and water (2:1) to give 4.7 g of the desired product, m.p. 179°-180° C.

Analysis for $C_{11}H_{10}ClNO_4$ Calculated, C, 51.68; H, 3.94. Found: C, 51.80; H, 4.00.

EXAMPLE 22

(E)[2-Methoxy-4-(2-nitro-1-propenyl)phenoxy]acetic acid

Step A: (2-Methoxy-4-formylphenoxy)acetic acid

Vanillin (16.3 g, 0.107 mole), ethyl bromoacetate (21.6 g, 0.128 mole), potassium carbonate (17.8 g, 0.128 mole) and N,N-dimethyl-formamide (75 ml) were united, stirred and heated at 50°-55° C. for 35 minutes. Then a 10% aqueous sodium hydroxide solution (100 ml) and water (300 ml) was added and the mixture stirred on a steam bath for one hour. The solution was cooled and acidified with hydrochloric acid. The solid that separated was removed by filtration, washed with water and dried to give 20.4 g of the desired product, m.p. 177°-178° C.

Step B: (E) [2-Methoxy-4-(2-nitro-1-propenyl)-phenoxy]acetic acid (2-Methoxy-4-formylphenoxy)acetic acid (10.5 g, 0.05 mole), butylamine (14.6 g, 0.2 mole) and benzene were united and refluxed in a flask equipped with a Dean-Stark water separator. The mixture was refluxed for 4 hours and then the benzene removed by distillation at reduced pressure. The residue consisted of 2-methoxy-4-(butyliminomethylene)-phenoxy)acetic acid which was treated with nitro-propane (17.8 g, 0.2 mole) and acetic acid (50 ml) and heated to boiling. After standing for 30 minutes the mixture was poured into crushed ice and acidified with hydrochloric acid. The solid that separated was removed by filtration, washed with water, dried and recrystallized first from a mixture of water and isopropyl alcohol (3:1) and then from a mixture of benzene and hexane (4:3) to give product melting at 116°–117° C.

Anal. Calc. for $C_{13}H_{15}NO_4$: C, 55.51; H, 5.38 N, 4.95. Found: C, 55.82; H, 5.40; N, 4.66.

EXAMPLE 23

Dry filled capsules containing 150 mg of active ingredient

|  | Per Capsule |
|---|---|
| (E) 4-[2,3-Dichloro-4-(2-nitro-1-butenyl)phenoxy]butyric acid (Example 1) | 150 mg |
| Lactose | 447 mg |
| Magnesium stearate | 4 mg |
| Capsule (size no. 000) | 600 mg |

Example 1 compound is reduced to a No. 60 powder and then lactose and magnesium stearate are passed through a No. 60 bolting cloth onto the powder and the combined ingredients admixed for 10 minutes and then filled into a No. 1 dry gelatin capsule.

EXAMPLE 24

Dry filled capsules containing 50 mg of active ingredient

|  | Per Capsule |
|---|---|
| (E) [4-(2-Nitro-1-propenyl)phenoxy]-acetic acid (Example 20) | 50 mg |
| Lactose | 149 mg |
| Magnesium stearate | 1 mg |
| Capsule (size no. 1) | 200 mg |

(E) [4-(2-Nitro-1-propenyl)phenoxy) acetic acid is reduced to a No. 60 powder and then lactose and magnesium stearate are passed through a No. 60 bolting cloth onto the powder and the combined ingredients admixed for 10 minutes and then filled into a No. 1 dry gelatin capsule.

EXAMPLE 25

Dry filled capsules containing 150 mg of active ingredient

|  | Per Capsule |
|---|---|
| Example 7 compound | 150 mg |
| Lactose | 447 mg |
| Magnesium stearate | 4 mg |
| Capsule (size no. 1) | 600 mg |

Example 1 compound is reduced to a No. 60 powder and then lactose and magnesium stearate are passed through a No. 60 bolting cloth onto the powder and the combined ingredients admixed for 10 minutes and then filled into a No. 1 dry gelatin capsule.

EXAMPLE 26

Dry filled capsules containing 150 mg of active ingredient

|  | Per Capsule |
|---|---|
| Example 9 compound | 150 mg |
| Lactose | 447 mg |
| Magnesium stearate | 4 mg |
| Capsule (size no. 1) | 600 mg |

Example 1 compound is reduce to a No. 60 powder and then lactose and magnesium stearate are passed through a No. 60 bolting cloth onto the powder and the combined ingredients admixed for 10 mintues and then filled into a No. 1 dry gelatin capsule.

Similar dry-filled capsules can be prepared by replacing the active ingredient of the above example by any of the other compounds of this invention.

EXAMPLE 27

Parenteral Solution of Sodium (E)-4-[2,3-Dichloro-4-(2-nitro-1-butenyl)phenoxy]butyrate 250 mg of (E)-4-[2,3-dichloro-4-(2-nitro-1-butenyl)-phenoxy]butyric acid is dissolved in 3.1 ml of 0.1 N sodium bicarbonate and sufficient isotonic buffer to make a final volume of 10 ml. The water from all sources was pyrogen-free. The solution is sterilized by filtration.

EXAMPLE 28

Parenteral Solution of Sodium (E)-1-[2,3-Dichloro-4-(2-nitro-1-butenyl)phenoxy]cyclobutane-1-carboxylate 250 mg of (E)-1-[2,3-dichloro-4-(2-nitro-1-butenyl)-phenoxy]cyclobutane-1-carboxylic acid is dissolved in 31 ml of 0.1 N sodium bicarbonate and sufficient isotonic buffer to make a final volume of 100 ml. The water from all sources was pyrogen-free. The solution is sterilized by filtration.

EXAMPLE 29

Parenteral Solution of Sodium (E) 3-Chloro-4-(2-nitro-1-butenyl)benzoic acid

One gram of (E) 3-chloro-4-(2-nitro-1-butenyl) benzoic acid is dissolved in 40 ml of 0.1N sodium bicarbonate and sufficient isotonic buffer to make a final volume of 100 ml. The water from all sources is pyrogen-free. The solution is sterilized by filtration.

EXAMPLE 30

Parenteral Solution of Sodium N-{(E)-4-[2,3-dichloro-4-(2-nitro-1-butenyl)phenoxy]-butyryl}glycine Two grams of N-{(E)-4-[2,3-dichloro-4-(2-nitro-1-butenyl)phenoxy]butyryl}glycine is dissolved in 62 ml of 0.1N sodium bicarbonate and sufficient isotonic buffer to make a final volume of 100 ml. The water from all sources was pyrogen free. The solution is sterilized by filtration.

EXAMPLE 31

Parenteral Solution of Sodium
N-{(E)-1-[2,3-Dichloro-(4-(2-nitro-1-butenyl)phenoxy]-cyclobutane-1-carbonyl}

0.103 g of N-{(E)-1-[2,3-dichloro-4-(2-nitro-1-butenyl)phenoxy]cyclobutane-1-carbonyl}glycine is dissolved in 31 ml of 0.1N sodium bicarbonate and sufficient isotonic buffer to make a final volume of 100 ml. The water from all sources was pyrogen free. The solution is sterilized by filtration.

EXAMPLE 32

Sterile Solution of Sodium (E)-4-[2,3-Dichloro-4-(2-nitro-1-butenyl)phenoxy]butyrate for Extracorporeal Treatment of Red Blood Cells from Patients with Sickle Cell Anemia 1.0297 g of (E)-4-[2,3-Dichloro-4-(2-nitro-1-butenyl)phenoxy]butyric acid is dissolved 33 ml of 0.1N sodium bicarbonate and sufficient isotonic buffer to make a final volume of 100 ml. The water from all sources was pyrogen free. The solution is sterilized by filtration. This solution is 3 mM in active antisickling agent.

EXAMPLE 33

Sterile Solution of Sodium (E) [2-methoxy-4-(2-nitro-1-propenyl)phenoxy]acetate for Extracorporeal Treatment of Red Blood Cells for Patients with Sickle Cell Anemia One gram of (E) [2-methoxy-4-(2-nitro-1-propenyl) phenoxy]acetic acid is dissolved in 35.6 ml of 0.1N sodium bicarbonate and sufficient isotonic buffer to make a final volume of 100 ml. The water from all souces was pyrogen free. The solution is sterilized by filtration. This solution is 3.56 mM in active antisickling agent.

It will be appreciated that the present invention provides a method for treatment of sickle cell anemia patients so as to resist undesired sickle cell anemia crisis. The method may advantageously be employed as a prophylactic.

Whereas particular embodiments of the invention have been described above for purposes of illustration, it will be evident to those skilled in the art that numerous variations of the details may be made without departing from the invention as defined in the appended claims.

EXAMPLE 34

In order to confirm the effectiveness of these compounds in reducing the effect of sickle cell anemia, tests were performed. The materials were tested according to the assay ($C_{sat}$) developed by Hofrichter et al. (J. Hofrichter, P. D. Ross and W. A. Eaton, *Proc. Natl. Acad. Sci.* USA, 73 30–35, 1976). This assay involves deoxygenation of concentrated sickle hemoglobin with dithionite in the presence of different concentrations of the drugs being tested. Samples are then sealed in quartz epr tubes under anaerobic conditions and spun at about 150,000×g for about 2½ hours at about 35° C. in an ultracentrifuge. This procedure pellets the polymerized HbS (sickle hemoglobin) to the bottom of the tubes and the supernatant (soluble HbS) is measured in the laboratory as the cyanmethemoglobin derivative. The more active the compound the greater the solubility of HbS and the smaller the pellet size. Activity is reported as a ratio of the HbS solubility with the particular drug to HbS solubility with no drug i.e. control. The higher the ratio the greater degree of activity of the drug. The numbers in parentheses are % inverse in the solubility of HbS; again the higher the number, the greater the activity of the drug. The results of four compounds of this invention are presented in Table 1 as exemplary of the compounds of the invention.

TABLE 1

| Example Number of the Compound Tested | Ratio of the HbS Solubility with the Drug Compared to HbS Solubility Without Drug (% increase in Solubility) at the Concentrations Indicated | | | |
|---|---|---|---|---|
| | 3 mM | 5 mM | 7 mM | 9 mM |
| 1 | 1.037 (8) | 1.063 (14) | 1.069 (16) | 1.093 (21) |
| 20 | 1.058 (13) | 1.080 (19) | 1.080 (19) | 1.097 (28) |
| 21 | 1.052 (13) | 1.100 (26) | 1.106 (27) | 1.150 (39) |
| 22 | 1.092 (23) | 1.121 (30) | 1.153 (37) | 1.226 (55) |
| | 1.079 (19) | 1.136 (33) | 1.165 (40) | 1.188 (45) |

What is claimed is:

1. A compound of the general formula and pharmaceutically acceptable salts thereof:

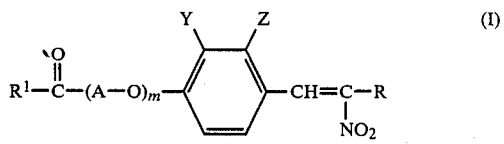

wherein:
$R^1$=HO or HOOC(CH$_2$)$_x$CHR$^2$NH—;
$R^2$=H, lower alkyl, benzyl or —CH$_2$OH;
x=0 or 1;
A=—(CH$_2$)$_n$—or

n=1 to 5; and
R=lower alkyl;
Y=H, Cl or OCH$_3$;
Z=H or Cl;
m=0 or 1;
with the proviso that where $R^1$=OH, Y is H or Cl and m is 1, then n is 4 or 5.

2. The compound of claim 1, wherein $R^1$ is OH, A is —(CH$_2$)$_4$—, R is C$_2$H$_5$, Y and Z are Cl and m is 1.

3. The compound of claim 1, wherein $R^1$ is OH, A is —(CH$_2$)$_5$—, R is C$_2$H$_5$, Y and Z are Cl and m is 1.

4. The compound of claim 1, wherein $R^1$ is OH, A is

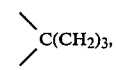

R is C$_2$H$_5$, Y and Z are Cl and m is 1.

5. The compound of claim 1, wherein A is

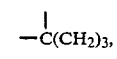

R is CH$_2$CH$_2$CH$_3$, Y and Z are Cl and m is 1.

6. The compound of claim 1, wherein $R^1$ is $HOOCCH_2NH$, A is $-(CH_2)_3-$, R is $C_2H_5$, Y and Z are Cl and m is 1.

7. The compound of claim 1, wherein $R^1$ is $S(+)$-$HOOCCH(CH_3)NH-$, A is $-(CH_2)_3-$, R is $C_2H_5$, Y and Z are Cl and m is 1.

8. The compound of claim 1, wherein $R^1$ is $S(+)$-$HOOCCH[CH_2CH(CH_3)_2]NH-$, A is $-(CH_2)_3-$, R is $C_2H_5$, Y and Z are Cl and m is 1.

9. The compound of claim 1, wherein $R^1$ is $S(+)$-$HOOCCH(CH_2OH)NH-$, A is $-(CH_2)_3-$, R is $C_2H_5$, Y and Z are Cl and m is 1.

10. The compound of claim 1, wherein $R^1$ is $S(-)$-$HOOCCH(CH_2C_6H_5)NH-$, A is $-(CH_2)_3-$, R is $C_2H_5$, Y and Z are Cl and m is 1.

11. The compound of claim 1, wherein $R^1$ is $HOOCCH_2NH-$, A is $-(CH_2)_3-$, R is $CH_2CH_2CH_3$, Y and Z are Cl and m is 1.

12. The compound of claim 1, wherein $R^1$ is $HOOCCH_2NH-$, A is

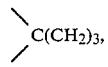

R is $C_2H_5$, Y and Z are Cl and m is 1.

13. The compound of claim 1, wherein $R^1$ is $HOOCCH_2NH$, A is $-(CH_2)_2-$, R is $C_2H_5$, Y and Z are Cl and m is 1.

14. The compound of claim 1, wherein $R^1$ is $HOOCCH_2NH-$, A is $-(CH_2)_4-$, R is $C_2H_5$, Y and Z are Cl and m is 1.

15. The compound of claim 1, wherein $R^1$ is $HOOCCH_2NH-$, A is $-(CH_2)_5-$, R is $C_2H_5$, Y and Z are Cl and m is 1.

16. The compound of claim 1, wherein $R^1$ is $HOOCCH_2CH_2NH$, A is

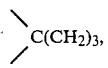

R is $C_2H_5$, Y and Z are Cl and m is 1.

17. The compound of claim 1, wherein $R^1$ is OH, Y is $OCH_3$, Z is H, R is $CH_3$, A is $CH_2$ and m is 1.

18. An anti-sickling pharmaceutical composition comprising a pharmaceutical carrier and an anti-sickling agent of the general formula and pharmaceutically acceptable salts thereof:

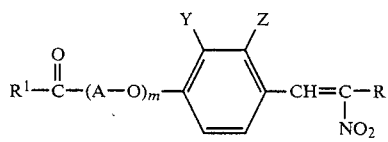

wherein:

$R^1$ = HO or $HOOC(CH_2)_xCHR^2NH-$;
$R^2$ = H, lower alkyl, benzyl or $-CH_2OH$;
x = 0 or 1;
A = $-(CH_2)_n-$ or

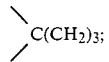

n = 1 to 5; and
Y = H, Cl or $OCH_3$;
Z = H or Cl;
m = 0 or 1; with the proviso that where $R^1$ = OH, Y is H or Cl and m = 1, then n is 4 to 5;
R = lower alkyl.

19. A method of treating a person for sickle cell anemia comprising administering to the person a therapeutically effective dosage of a compound of the general formula and pharmaceutically acceptable salts thereof: wherein:

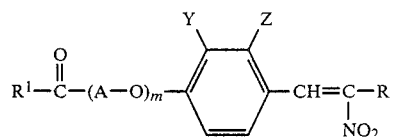

wherein:
$R^1$ = HO or $HOOC(CH_2)_xCHR^2NH-$;
$R^2$ = H, lower alkyl, benzyl or $-CH_2OH$;
x = 0 or 1;
A = $-(CH_2)_n-$ or

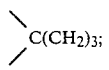

n = 1 to 5; and
Y = H, Cl or $OCH_3$
Z = H or Cl
m = 0 or 1
R = lower alkyl.

20. The compound of claim 1, wherein $R^1$ is OH, Y is H, Z is Cl, R is $C_2H_5$ and m is 0.

21. The antisickling compositon of claim 18 wherein the antisickling agent is the compound wherein $R^1$ is OH, Y and Z are H, A is $CH_2$, R is $CH_3$ and m is 1.

22. The method of treating a person for sickle cell anemia comprising administering to the person a therapeutically effective dosage of the compound of claim 19 wherein $R^1$ is OH, Y and Z are H, A is $CH_2$, R is $CH_3$, and m is 1.

23. The method of treating a person for sickle cell anemia comprising administering to the person a therapeutically effective dosage of the compound of claim 19 wherein $R^1$ is OH, Y and Z are Cl, A is $(CH_2)_3$, R is $C_2H_5$ and m is 1.

* * * * *